United States Patent [19]

Bar-Issac et al.

[11] 3,947,120
[45] Mar. 30, 1976

[54] GEM IDENTIFICATION

[75] Inventors: Charles Bar-Issac, Ramat Gan; Ephraim Frei; Shmuel Shtrikman, both of Rehovot, all of Israel

[73] Assignee: Yeda Research and Development Co. Ltd., Rehovot, Israel

[22] Filed: Oct. 2, 1974

[21] Appl. No.: 511,383

[30] Foreign Application Priority Data
Oct. 23, 1973  Israel.................................. 43465

[52] U.S. Cl................................. 356/30; 356/209
[51] Int. Cl.$^2$....................................... G01N 21/00
[58] Field of Search ............... 356/30, 31, 209, 212

[56] References Cited
UNITED STATES PATENTS

| | | | |
|---|---|---|---|
| 1,799,604 | 4/1931 | Read..................... | 356/30 |
| 3,715,165 | 2/1973 | Smith.................... | 356/209 X |
| 3,740,142 | 6/1973 | Takubo.................. | 356/30 |
| 3,858,979 | 1/1975 | Elbe...................... | 356/30 |

Primary Examiner—Archie R. Borchelt
Assistant Examiner—E. R. La Roche
Attorney, Agent, or Firm—Browdy and Neimark

[57] ABSTRACT

A device and method for obtaining an identification pattern of polished gemstones. The device comprises, in combination, means for holding the gemstone in a reproducible position, means for creating a collimated parallel light beam, a lens for projecting a pattern obtained by reflecting the collimated parallel light beam from the gemstone onto a plane recording medium facing a plane reference surface of the gemstone. The distinctive pattern may be projected onto the plane recording medium via beam-splitting means. The light used can be white, or monochromatic. Polarized light may be used. Rotation of the pattern about the reference point of the optical axis provides a pattern which may be evaluated automatically.

21 Claims, 6 Drawing Figures

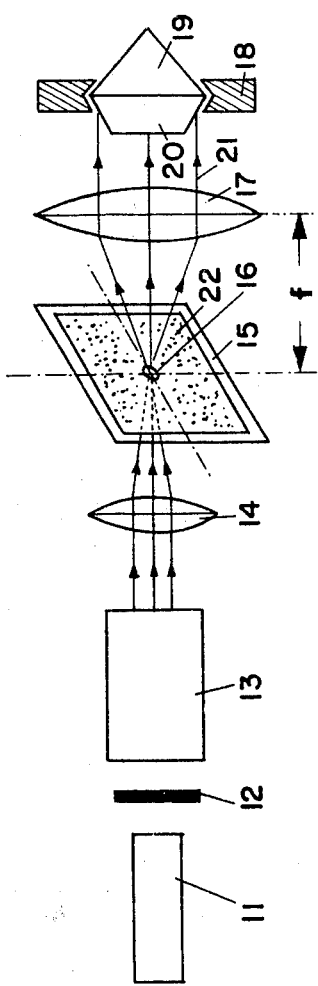
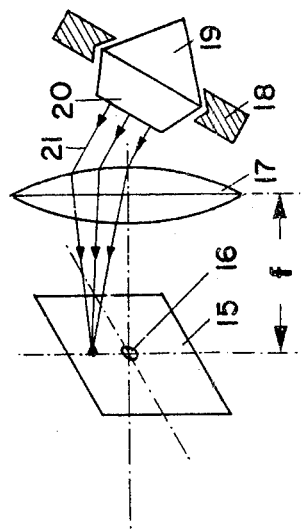

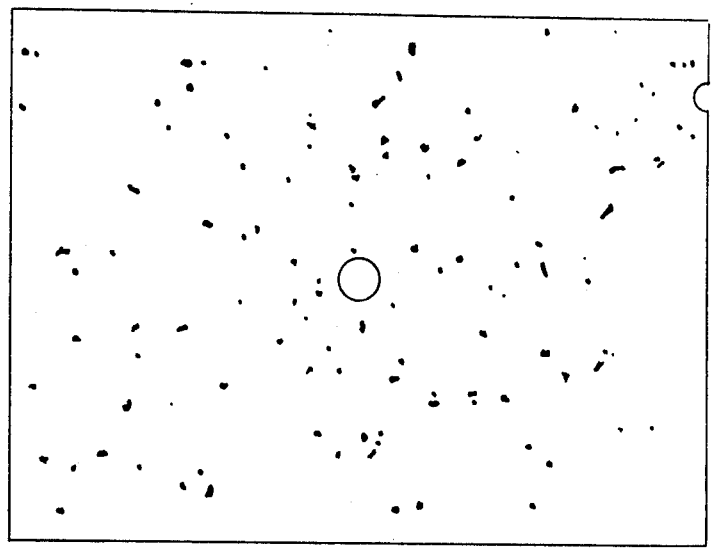
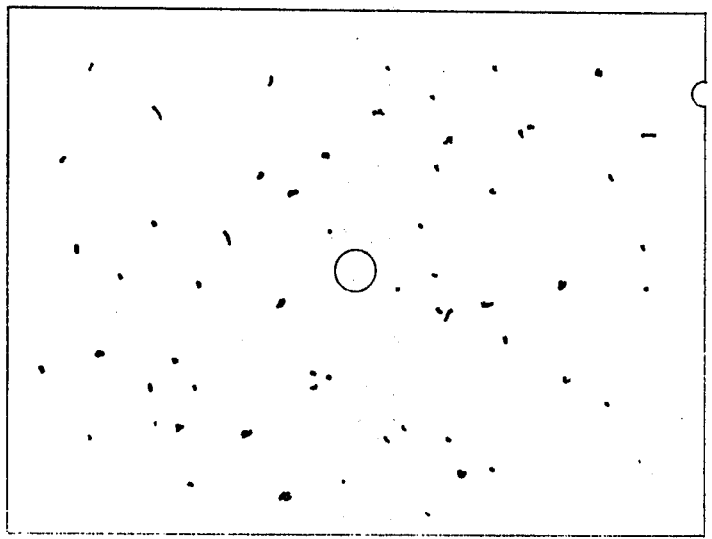
Fig.3

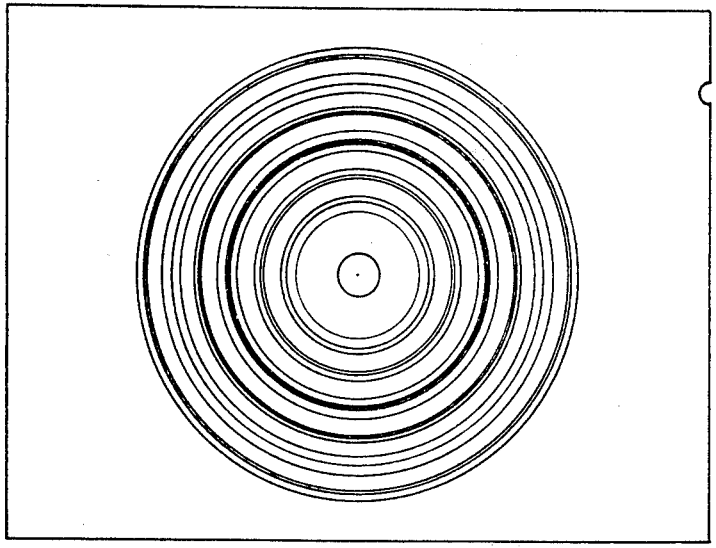
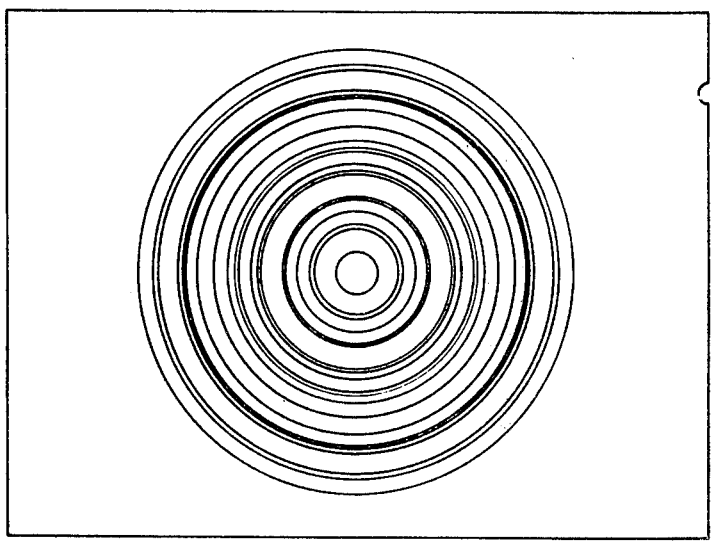
Fig.4

GEM IDENTIFICATION

BACKGROUND OF THE PRESENT INVENTION

Genuine gem-stones, such as diamonds, sapphires, emeralds and the like are of considerable value and it is of considerable interest to provide means for the positive indentification of an individual gem. This is of value for the owner who purchases the specific gem and can thus be given a certificate identifying his gem; it is of importance in cases when a gem is lost or stolen, and such positive records of identification can be used in Court as proof of identification. It is likely that insurance companies will find much interest in positive means of identification of gem stones, and other further features of the invention will become apparent hereinafter. The identification pattern according to the invention ought to be included in the insurance file of each gemstone. When gems are offered through middlemen, the recorded identification pattern makes possible a positive identification of each gemstone. Certificates issued for certain gems ought to be in conjuction with record patterns.

STATE OF THE PRIOR ART

The identification of gem-stones is rather difficult, and only recently a commercial firm has offered a service of identification based on the Nomarski differential interference contrast. This record is obtained at a high magnification and the procedure is comparatively complicated.

There is known a device for discriminating or identifying jewels, which comprises obtaining a record of light-beams refracted and reflected on a light-sensitive material, said light-sensitive material surrounding the holding means of the jewel. The record obtained according to this known method comprises a plurality of spots resulting from the regular pattern of the cut and polished gem; this cannot be evaluated by simple automatic means.

SUMMARY OF THE PRESENT INVENTION

The present invention relates to a novel device for the identification of polished diamonds and other similar polished gems. More particularly, the present invention relates to a device for obtaining a permanent record of polished diamonds and other gems, comprising a plurality of spots resulting from internal refraction and reflection of light rays due to imperfections of such polished gems. The term "imperfections" relates both to imperfections in the crystal structure of the gem as well as to imperfections of the polished surfaces of same. The present invention further relates to a device for obtaining records of identification which can be evaluated and compared automatically, as for example by the use of a scanning device in combination with a computer. Furthermore the invention relates to a method for recording a distinctive pattern resulting at least in part from internal refractions and possible multiple reflections and due to imperfections of the gem. According to a further embodiment of the invention, means are provided for holding the stone in such a manner as to obtain a record which is substantially invariant as regards rotational changes of same. It further relates to a method of converting such pattern into a form which can be evaluated with the aid of a scanning device and a computer. Other and further features of the present invention will become apparent hereinafter.

Contrasted with the known methods, the method according to the present invention is a very simple and straightforward one, and by means of a quite simple apparatus records can be obtained. The production of these is not expensive and thus the method can be widely used. Furthermore, the record can be easily converted into a form which can be evaluated by mechanooptical means, in combination with a computer.

The present invention will be described in the following with reference to diamonds, and especially with reference to diamonds having the standard brilliant cut. It is clear that this is by way of example only and that the method is applicable as well to other diamond cuts and to other polished gemstones. Practically all of these have a preferred plane surface which can be used as reference surface, as will be set out hereinafter.

The present invention comprises a novel device for obtaining permanent record of a "fingerprint" of gemstones, this device comprises an optical system adapted to provide a plurality of reflections reflected from the gemstone and means for recording the reflections. At least part of these result from internal reflections due to imperfections. Means are provided for a reproducible positioning of the diamond the pattern of which is recorded. In the case of the brilliant-cut, the front surface ("table") is used as reference surface. There exists the possibility to record reflections at varying angles, and the results obtained by using varying angles are different:

a. If the diamond is positioned at such an angle that at least some of the direct reflections from the lateral facets of the crown reach the recording medium facing the stone, the pattern will comprise also some reflections which are indicative of the symmetry of the polished gem, and these facilitate the subsequent identification of such gem. This pattern contains always also the spots due to internal reflections, (and when white light is used: spots due to dispersion of light); at least part of these being due to the imperfections of the gem.

b. If small angles are used, none of the reflections from the lateral facets of the crown will reach the recording medium facing the stone, and in this case the recorded pattern is due only to internal reflections, the character of which is due to a large extent to imperfections of the polished surfaces and to internal imperfections. It is assumed that these are due to internal scattering of the light in the diamond, and also due to imperfections of the stone and/or its cut and polished surfaces. The small-angle reflections are a very sensitive indicator of even slight imperfections in the diamond, and these result in a specific pattern which is unique for each polished gemstone.

According to a specific embodiment of the present invention, a permanent record is produced which is adapted to be compared by means of automatic means of scanning. This is accomplished by rotating the record comprising the plurality of spots about the optical axis and recording the resulting pattern of a plurality of circles. These are of a definite distribution and intensity, corresponding to each of the spots on the original record. This pattern can also be obtained directly by a time-exposure of the pattern while the recording medium and the stone are rotated respective each other about the optical axis. This record of a plurality of circles makes possible to compare various records by automatic means and also to resort to the use of a computer for the evaluation and comparison of such records. The record obtained is invariant as regards rotation about its center of rotation. This makes possible the automatic evaluation of the recorded pattern. It is advantageous to record both a "rotated pattern" for automatic preliminary identification, and also a stationary pattern for a final evaluation of the results obtained, as the stationary pattern contains more accurate details which may be used for the final indentification.

Monochromatic light, a combination of certain colors, white light, or polarized light may be used for obtaining the pattern. If monochromatic light is used, the pattern is due to reflections, comprising multiple internal reflections and refractions; if there is used white light, or a combination of colors, the individual spots of the pattern are due also to refractions of different wave lengths, and each spot has a certain direction and size, comprising various colors. When recorded on colour-film the color-spots provide additional means of identification.

The device for obtaining permanent records of reflections from polished gemstone is described by way of example only with reference to the enclosed schematical drawings, which are not according to scale and in which:

BRIEF DESCRIPTION OF THE DRAWINGS

FIG. 1 is a schematical side wiew, with film-holder in perspective;

FIG. 2 is an illustration of the vertical alignment of the table of a gemstone or other reference surface reflecting the light beam;

FIG. 3 and 3' are records obtained on a recording medium by means of the device of FIG. 1;

FIG. 4 and 4' are records obtained by rotating records of the type set out in FIG. 3 and 3';

DESCRIPTION OF THE PREFERRED EMBODIMENT

Figure 5:
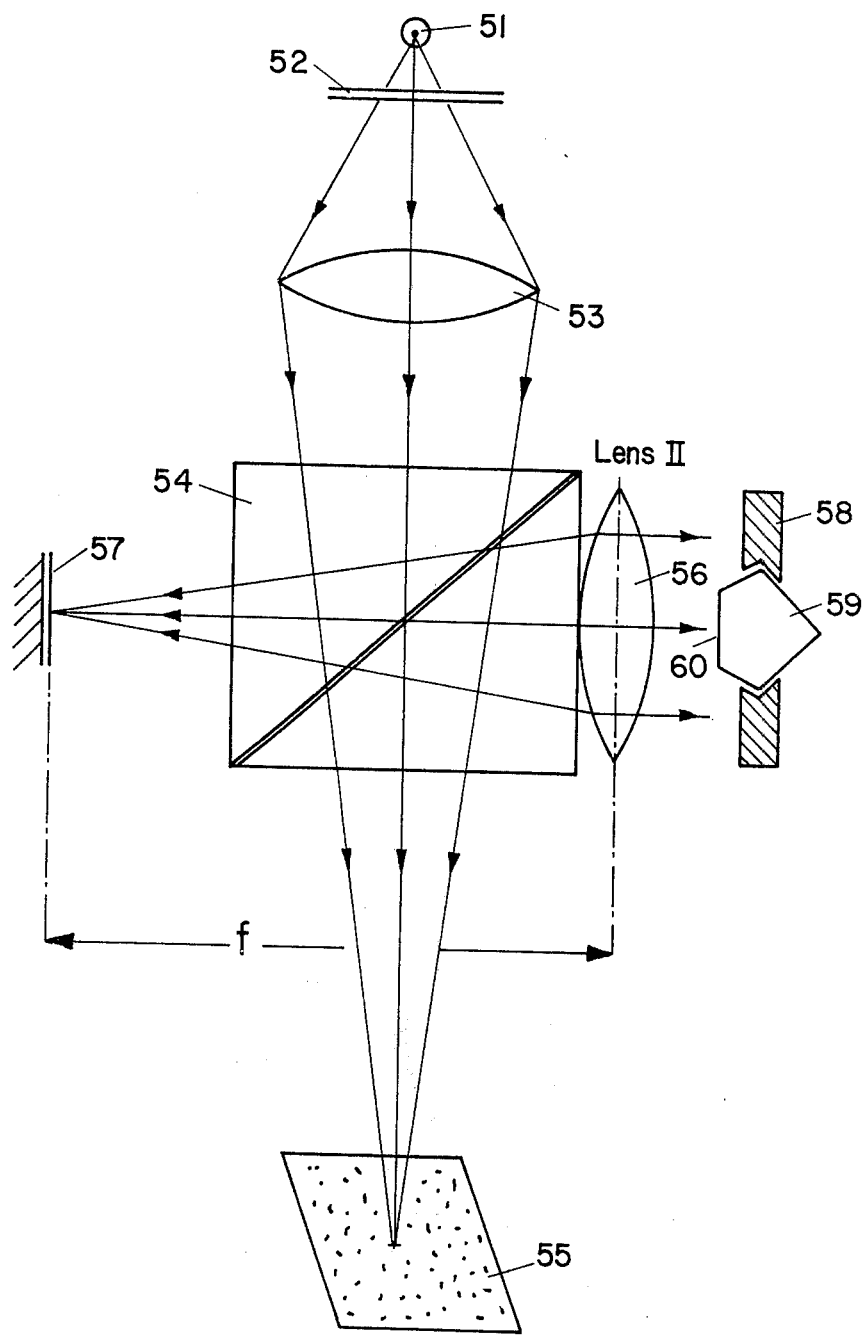
FIG. 5 is a schematical side view of another device according to the present invention.

The device for obtaining the identification record of the gemstone (in the following: diamond) comprises essentially means for positioning the gem-stone so as to have a preferred defined surface thereof perpendicular to a collimated beam of light, means for projecting reflections from the diamond onto a recording medium facing the gemstone and obtaining a record of the pattern of reflections.

As shown in FIG. 1, a device according to the invention comprises a light-source 11, a shutter 12, a collimator 13, a lens 14, a screen 15, at the focal plane of lens 14, provided with a small central pinhole 16, a second lens 17, at a distance of its focal length from said screen 15, and means 18 for holding the diamond 19 with its table 20 perpendicular to the collimated beam of light 21.

The diamond is advantageously positioned quite close to the lens (nearly touching it). When a wide-angle lens is used a pattern is obtained which includes also spots due to reflections from the regular facets.

On the side of the screen 15 facing the diamond, recording means 22 are provided, preferably being a photographic film in a suitable holder or light-sensitive paper or the like. The holder 18 is preferably eccentrical, and as shown in FIG. 2 this provides for the possibility to adjust the position of the diamond by turning the holder in such a manner that the light reflected from the table and focused by lens 17 will be collimated onto pinhole 16. This provides the possibility to repeat the record with entirely identical results if the same optical system is used.

Advantageously, a laser or a number of lasers are used as light source, and the collimated beam is focused by lens 14, passes through the pinhole 16, and after the lens 17 a parallel beam is obtained which is perpendicular to the table 20 of the diamond 19. The diamond is adjusted so that the reflections from the table are focused onto the pinhole 16. At the same time reflections resulting from internal reflections and refractions result in the projection, by lens 17, of a distinctive pattern on the recording medium 22. In actual use, the diamond is first positioned in its exact location, and after this the recording medium is exposed and a record of the pattern is made by the use of the shutter 12.

According to a preferred embodiment of the invention there is used a vertical arrangement of the entire device, in the direction shown in FIG. 1. in which case there is used instead of the holder 18 a plane polished glass plate 18', which is in a horizontal position. On this the gem is positioned, its table touching the glass surface. The gem is positioned in such a manner that its center will be exactly above the pinhole in the screen facing it.

It is possible to record an indentification pattern according to the present invention without resorting to the use of a recording medium with a central hole as illustrated above. This embodiment avoids the necessity of punching the hole and also the exact alignment of the punched film. This embodiment, illustrated in FIG. 5 and 6, makes use of beam splitting elements such as cube prisms or pellicles.

With the two embodiments shown in these Figures, the alignment is according to some reference point provided by the optical system.

As shown in FIG. 5, the device according to the invention comprises in combination a light-source 51, a shutter 52, a lens 53, a cube beam splitter 54, a film 55 shown in perspective view, a lens 56, a mirror 57 and gem holder 58 holding the gem 59 with the reference surface 60 facing the lens 56. The path of the light beam is indicated schematically, and it is clear that the beam is partially reflected onto mirror 57, via lens 56 onto the reference surface of the gem 59, and onto the film 55, where the pattern is recorded.

Figure 6:
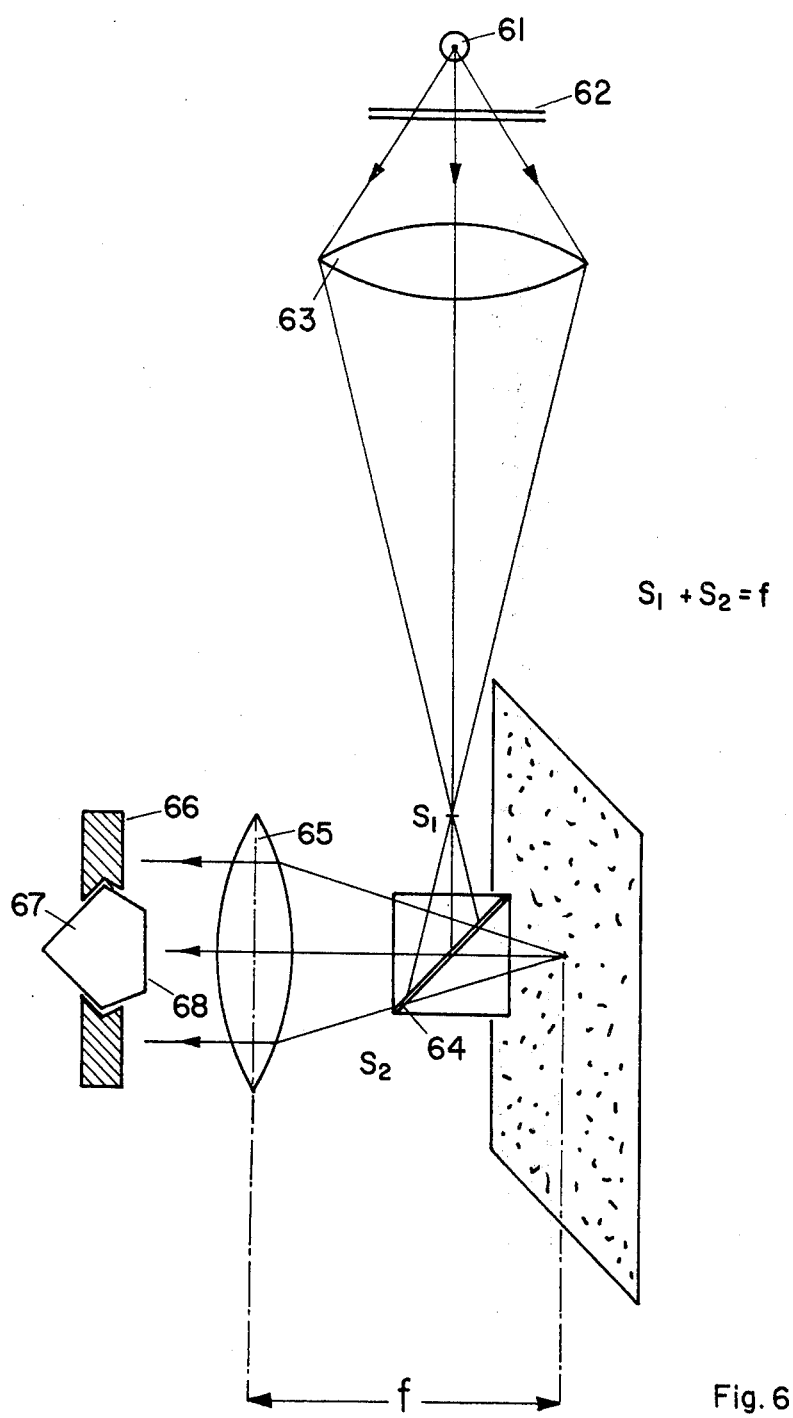
FIG. 6 is a schematical side view of yet a further embodiment of a device according to the present invention.

A similar arrangement is shown in FIG. 6, wherein 61 is a light source, 62 a shutter, 63 a lens, 64 a pellicle used for beam splitting, 65 a lens, 66 the lens holder with gem 67, having the reference plane 68 facing lens 66. The path of the light beam is indicated, and it is clear that the pellicle reflects the light onto the reference plane and that the resulting pattern is recorded on the recording medium, shown in perspective, 69.

It is within the ambit of the present invention to use an arrangement wherein the collimated light beam is directed onto the gemstone from the opposite direction, i.e. onto the apex of the pavilion, and the pattern of reflections and/or refractions resulting is recorded.

If white light is used, there are obtained colored spots, varying in size and degree of dispersion. When recorded on a recording medium reproducing the colors, these provide additional details of identification.

When polarized light is used in conjunction with a suitable analyzer, further special effects are obtained due to the sensitivity and selectivity of polarized light in multiple reflections through several different angles. The direction of initial polarization and of the analyzer can be varied, resulting in different identification patterns characteristic of each gem. As to the optical effects with polarized light, see Born & Wolf, Principles of Optics, 2nd Ed. Pergamon Press, London, 1964, p. 36–51.

In order to facilitate the comparison of existing records with a pattern recorded, it is advantageous to obtain a pattern by rotating a pattern of the type shown in FIG. 3 and 3', resulting in a plurality of circles of varying intensity. After a preliminary comparison by means of this type of record, the original records can be compared in order to provide for a positive and final identification. Such patterns are described in FIG. 4 and 4'. It is clear that the above is by way of example only and that many modifications and changes in the nature and arrangement of parts may be resorted to without departing from the scope and spirit of the present invention.

We claim:

1. A device for obtaining a reproducible identification pattern of a polished gemstone, comprising, in combination:
    light directing means for creating a parallel light beam and directing the light beam onto the gemstone, said light directing means including light source means for providing a parallel light beam, a first focusing lens in the path of the light beam for focusing the light beam onto a focal point, and a second lens located downstream of said focal point in the path of the light beam at an optical path distance from said focal point equal to the focal length of said second lens;
    holding means disposed downstream of said second lens for holding the gemstone in the path of the light beam with a plane reference surface thereof at a defined reproducible angle to the parallel light beam directed thereon through said second lens; and
    a screen optically located on the opposite side of said second lens as the gemstone at an optical path distance from said second lens equal to the focal length thereof, whereby said screen receives reflections from the gemstone passing through said second lens.

2. A device in accordance with claim 1 wherein said light source means comprises a light source and a collimator.

3. A device in accordance with claim 1 wherein said screen is located at the focal point of said first lens, said screen having a pinhole therethrough at said focal point.

4. A device in accordance with claim 1 further including shutter means between said light source and said first lens for obtaining a beam of light for a predetermined period of time.

5. A device in accordance with claim 1 wherein said light source means includes a source of monochromatic light.

6. A device in accordance with claim 1 wherein said light source means includes a source of polarized light.

7. A device in accordance with claim 1 wherein said light source means includes a source of white light.

8. A device in accordance with claim 7 wherein said light source means further includes a suitable light filter in the path of said white light.

9. A device in accordance with claim 1 wherein said light source means includes a laser.

10. A device in accordance with claim 3 further including means connected to said holding means for focusing the reflection from the plane reference surface of the gemstone onto the pinhole of said screen.

11. A device in accordance with claim 3 further including a light sensitive recording medium positioned on the side of said screen optically facing the gemstone.

12. A device in accordance with claim 1 further including beam splitting means between said first and said second lenses for splitting the beam into a first portion reflected at an angle and a second portion passing therethrough without reflection, said screen being located in the path of one of said portions and said focal point of said first lens being in the path of the other of said portions.

13. A method for recording distinctive patterns for the identification of polished gemstones, comprising:
    directing a beam of light through a lens for creating a parallel beam of light;
    holding the polished gemstone with a plane reference surface thereof at a defined reproducible angle to the parallel light beam coming from the lens; and
    recording a pattern of reflections returning through the lens on a plane light sensitive recording medium located at an optical path distance from the lens equal to the focal length thereof.

14. A method in accordance with claim 13 wherein the parallel beam of light is of monochromatic light.

15. A method in accordance with claim 13 wherein the parallel beam of light is of polarized light.

16. A method in accordance with claim 13 wherein the beam of light directed toward the lens comes from a source of a parallel beam of light which has passed through an initial lens for focusing the light onto a focal point and wherein the lens for creating a parallel beam of light is at optical path distance from the focal point equal to the focal length thereof.

17. A method in accordance with claim 13 wherein the reflections returning through the lens are directed onto the recording medium through a beam-splitting means.

18. A method in accordance with claim 13 wherein the gemstone is a diamond of brilliant cut and wherein the plane reference surface of the gemstone is the table of the diamond.

19. A method in accordance with claim 13 wherein said recording step is a time exposure while effecting a relative rotation of the recording medium and the gemstone over a total revolution, resulting in a pattern comprising a plurality of concentric circles of varying intensity.

20. A method in accordance with claim 19 wherein said relative rotation comprises rotating the recording medium about the optical axis of the pattern of reflections over a total revolution, 21. A method in accordance with claim 19 wherein said relative rotation comprises rotating the gemstone about the optical axis of the pattern of reflections over a total revolution.

* * * * *